(12) United States Patent
Shiomi et al.

(10) Patent No.: US 7,988,629 B2
(45) Date of Patent: Aug. 2, 2011

(54) CEREBRUM EVALUATION DEVICE

(75) Inventors: Kakuichi Shiomi, Tokyo (JP); Susumu Kobayashi, Mito (JP); Michiko Takaoka, Tokyo (JP); Hitoshi Abe, Tokyo (JP); Michiko Okiyama, Tokyo (JP)

(73) Assignees: Electronic Navigation Research Institute, An Independent Administrative Institution, Tokyo (JP); Kakuichi Shiomi, Toyko (JP); Susumu Kobayashi, Tokyo (JP); Michiko Takaoka, Tokyo (JP); Hitoshi Abe, Tokyo (JP); Michiko Okiyama, Tokyo (JP)

( * ) Notice: Subject to any disclaimer, the term of this patent is extended or adjusted under 35 U.S.C. 154(b) by 1014 days.

(21) Appl. No.: 11/587,634

(22) PCT Filed: Apr. 28, 2004

(86) PCT No.: PCT/JP2004/005663
§ 371 (c)(1),
(2), (4) Date: Aug. 22, 2007

(87) PCT Pub. No.: WO2005/104950
PCT Pub. Date: Nov. 10, 2005

(65) Prior Publication Data
US 2008/0132768 A1 Jun. 5, 2008

(51) Int. Cl.
*A61B 5/00* (2006.01)
*A61B 5/103* (2006.01)
*A61B 5/02* (2006.01)
*G06F 15/00* (2006.01)

(52) U.S. Cl. ......... 600/300; 600/587; 600/485; 704/200

(58) Field of Classification Search ........................ None
See application file for complete search history.

(56) References Cited

U.S. PATENT DOCUMENTS

| | | | |
|---|---|---|---|
| 7,363,226 B2 | 4/2008 | Shiomi et al. | |
| 7,737,859 B2 | 6/2010 | Takaoka et al. | |
| 2003/0065241 A1 | 4/2003 | Hohnloser | |
| 2005/0065412 A1* | 3/2005 | Shiomi et al. | 600/300 |
| 2007/0174377 A2 | 7/2007 | Shiomi et al. | |

(Continued)

FOREIGN PATENT DOCUMENTS

EP     1 454 586 A1     9/2004

(Continued)

OTHER PUBLICATIONS

Shiomi, K., "Chaotic Voice Analysis and Model of Cerebral Dynamics," Journal of Kansei Engineering, Collected Papers of Japan Society of Kansei Engineering, vol. 4, No. 1, pp. 3-12, (Feb. 2004).

*Primary Examiner* — Henry M Johnson, III
*Assistant Examiner* — Shirley Jian
(74) *Attorney, Agent, or Firm* — Finnegan, Henderson, Farabow, Garrett & Dunner, L.L.P.

(57) ABSTRACT

There is provided a cerebrum evaluation device for evaluating the state of the cerebrum of a subject by analyzing a speech signal of the subject by using chaotic signal processing utilizing the periodicity of the signal. The cerebrum evaluation device evaluates the state of the cerebrum according to the speech signal uttered by the subject. The cerebrum evaluation device includes: a statistic information database containing chaotic index values of speech signals of a plurality of subjects; a speech signal acquisition unit for acquiring a speech signal; a chaotic index value calculation unit for calculating a chaotic index value of the speech signal by the chaotic signal processing utilizing the periodicity of the speech signal acquired; an evaluation unit for evaluating the state of the cerebrum of the subject according to the calculated chaotic index value by referencing the statistic information database; and an output unit for outputting the result evaluated by the evaluation unit.

7 Claims, 6 Drawing Sheets

FOREIGN PATENT DOCUMENTS

| | | |
|---|---|---|
| JP | 2002-306492 | 10/2002 |
| JP | 2003-79602 | 3/2003 |
| JP | 2003-144438 | 5/2003 |
| JP | 2003-280684 | 10/2003 |
| WO | WO 03/041589 A1 | 5/2003 |
| WO | WO 2004/075074 A1 | 2/2004 |

* cited by examiner

CEREBRUM EVALUATION DEVICE

TECHNICAL FIELD

The present invention is related to a cerebrum evaluation device for measuring and evaluating the activity of the cerebrum of a subject by using a chaotic signal processing method using the periodicity of the speech signal of the subject to analyze the speech signal.

BACKGROUND ART

There is known that the cerebrum activity of a subject can be measured by the chaotic analysis of the speech signal of the subject. Some exemplary processing devices are disclosed in JP-A-2001-348108 (patent reference #1), JP-A-2002-82734 (patent reference #2), JP-A-2001-116408 (patent reference #3), and JP-A-2001-280105 (patent reference #4).

The inventions disclosed in the patent references cited above attempt to obtain a biological signal of a subject including the speech signal to process the signal in accordance with a chaotic signal processing method in order to analyze and diagnose.

The devices and systems using the chaotic processing method as disclosed in the patent references cited above use any one of chaotic analysis well known in the art including such as Wolf's algorithm, Kantz' algorithm, Rosenstein's algorithm, Worel's algorithm, and Sano-Sawada's algorithm.
patent reference #1: JP-A-2001-348108
patent reference #2: JP-A-2002-82734
patent reference #3: JP-A-2001-116408
patent reference #4: JP-A-2001-280105

DISCLOSURE OF THE INVENTION

The Problem to be Solved by the Invention

In the prior art as have been described above, in particular, the device disclosed in the patent reference #1 cited above, has the object to obtain and evaluate the voice signal uttered by imposing a load which is intentional to and recognizable by the subject. The load intentional to the subject is applied because the application of the load to the subject increases to the maximum the activity of the cerebrum of the subject, and the measurement of the maximum limit value contributes to the evaluation of the activity of cerebrum of the subject, more specifically, to evaluate and diagnose the state of cerebral diseases.

In the study of one of the inventors in recent years (Kakuichi SHIOMI, "Cerebral Function Model considered based on Speech Analysis", Journal of Kansei Engineering, Collected Papers of Japan Society of Kansei Engineering, vol. 4, no. 1, February 2004, p. 3-p. 12), the speech signal uttered by a subject has been shown to include the speech signal and some noises which disturb the chaoticity of the speech signal (the noise here is the noise generated in the signal transmitted between the cerebral areas when the subject speaks. In accordance with the study of one of the inventors of the present invention, it is suggested that the noise is generated along with the signals exchanged between the Wernicke's area and the Broca's area and the signals within those areas). It is thought that the chaoticity of the speech signal does not vary itself whether or not the subject is applied with a load and that the noise part thereof varies by imposing the load.

In accordance with the cerebral function model of the above consideration, the application of load recognizable by the subject in the prior art is no more than increasing the noise.

In other words, the prior art does perform chaotic analysis of a speech signal including the noise and does not perform the chaotic analysis of the speech signal intrinsic to the subject. Moreover, the prior art may not obtain any significant value for effective analysis because the speech signal is a system that the dynamics changes along with the time, as have been described above.

The chaotic analysis of the prior art described above assumes that the object of the analysis is a system having the stable dynamics (dynamics is the behavior limited by the physical shape, or the property which provides the behavior). Therefore, in a system such as the speech signal in which the dynamics changes along with the time, temporally local first Lyapunov exponent, or the Lyapunov spectrum as in the Sano-Sawada's algorithm cannot be calculated as a significant value.

A system with the stable dynamics is the one in which the physical arrangement or length does not vary, and in case when such a system shows some chaotic behavior, the shape of the strange attractor generated by the time-series signal given by the system will have a similar form. In addition, an exemplary system in which the dynamics changes along with the time is the system of speech vocal organ of a living body, in which the physical arrangement or the length changes. When pronouncing /a/ phoneme and /o/ phoneme, for example, the shape from the throat to oral cavity is different, and the strange attractor generated by the speech signal has a different form.

The speech signal, on the other hand, is thought of a time-series signal to be generated by a system with the dynamics changing along with the time, because of many factors such as that the shape from the throat to the oral cavity changes when speaking as have been described above. The chaotic analysis methods of the patent references as cited above, which assume the chaotic analysis in a system with the dynamics stable along with the time, therefore cannot calculate the processing result as significant value, thus cannot be effective analysis.

Means for Solving the Problem

The inventors of the present invention has invented a cerebrum evaluation device for measuring and evaluating the activity of the cerebrum of a subject, by obtaining the speech signal uttered by the subject, which signal is a time-series signal of a system with the dynamics changing along with the time, and by performing chaotic analysis on the speech signal by using the chaotic signal processing method, invented by the inventors of the present invention, using the periodicity of the speech signal.

In the chaotic signal processing using the periodicity of the speech signal implemented in the cerebrum evaluation device in accordance with the present invention is capable of performing relative evaluation of the intensity of the chaoticity and the intensity of the noise that disturbs the chaoticity, so that the load recognizable by the subject is not needed to be applied, as shown in the patent reference #1.

The invention set forth in claim 1 provides a cerebrum evaluation device for evaluating the status of cerebrum by the speech signal uttered by the subject. The cerebrum evaluation device comprises a statistic information database containing chaotic index values of speech signals of a plurality of subjects; a speech signal acquisition unit for acquiring said speech signal; a chaotic index value calculation unit for calculating a chaotic index value of said speech signal by chaotic signal processing using the periodicity of said acquired speech signal; an evaluation unit for evaluating the cerebral state of said subject from said calculated chaotic index value by referencing said statistic information database; and an output unit for outputting the result evaluated by said evaluation unit.

In accordance with the present invention, significant chaotic index values can be calculated based on the speech signal, which is a time-series signal of the system with the dynamics changing along with the time. The chaotic index value thus calculated may be compared with the statistic information on the chaotic index values of a plurality of subjects to coordinate the cerebral activity of the subject to the statistic data to evaluate (diagnose) the state of the cerebrum of the subject.

The invention set forth in claim 2 provides a cerebrum evaluation device for evaluating the state of the cerebrum by the speech signal uttered by a subject. The cerebrum evaluation device comprises a statistic information database containing time-sequentially the chaotic index values of the speech signal of said subject; a speech signal acquisition unit for acquiring said speech signal; a chaotic index value calculating unit for calculating the chaotic index value of said speech signal by acquired chaotic signal processing using the periodicity of said speech signal; an evaluation unit for evaluating the cerebral state of said subject from said calculated chaotic index value by referencing said statistic information database; and an output unit for outputting the result evaluated by said evaluation unit.

In accordance with the present invention, a significant chaotic index value can be calculated based on the speech signal, which is a time-series signal of the system with the dynamics changing along with the time. The change along with the time of the state of the cerebrum of the subject can be evaluated by storing sequentially the chaotic index value calculated of the subject, allowing the evaluation of the possibility of onset as well as the progress of a cerebral functional disease of the subject.

The invention set forth in claim 3 provides a cerebrum evaluation device, in which said speech signal acquisition unit obtains the speech signal sampled by an A/D converter from the speech signal obtained by a voice acquisition unit.

The voice of a subject is collected by a microphone. The speech signal thus acquired is analog signal, which is preferably converted to digital signal by an A/D converter for the chaotic analysis by the cerebrum evaluation device.

The invention set forth in claim 4 provides a cerebrum evaluation device, in which said statistic information database contains the chaotic index values of the speech signals of said plurality of subjects in relation with one or more of the race, age, gender of subject; said evaluation unit compares any one or more of race, age, gender of said uttering subject and the chaotic index value of the subject with the race, age, gender, and chaotic index value stored in said statistical information database to evaluate the state of the cerebrum of said subject.

When performing the chaotic examination of the speech signal in accordance with the present invention, the race, age, gender, and the like of the subject may be stored in relation with the chaotic index value so as to evaluate the state of the cerebrum of the subject with a higher precision.

The invention set forth in claim 5 provides a cerebrum evaluation device, in which said statistic information database stores the chaotic index values of the speech signal of said subject in relation with the aging information of the subject and the time-sequential change of the state of cerebral function disease, said evaluation unit evaluates the state of the cerebrum of said subject based on the time-sequential change of the chaotic index value of said subject.

When performing the chaotic examination of the speech signal using the present invention the time-sequential storage of chaotic index value of the subject allows profiling the time-sequential change of the subject.

The invention set forth in claim 6 provides a cerebrum evaluation device, in which said cerebrum evaluation device is connected to a speech voice acquisition environment generator unit for controlling the acquisition environment of said speech voice, and to an environment replaying unit for replaying the environment specified by said speech voice acquisition environment generator unit, said speech voice acquisition environment generator unit decides any one or more of the visual movie, still image, voice as the environment to be replayed for said subject, and said environment replaying unit replays the environment decided.

By using a speech acquisition environment generating apparatus as in the present invention to concentrate the conscience of the subject on the picture, image, and voice reproduced by the environment generating apparatus when acquiring the speech voice of the subject, the speech uttered by the subject can be made homogeneous. This allows the precision of the chaotic index value calculated by the cerebral evaluation device to be improved thereby.

Effect of the Invention

By using the present invention, the cerebral activity of the subject can be significantly chaotically evaluated based on the speech signal. Then the value thus measured can be compared with the statistic data of the cerebral activity previously recorded to infer the level of cerebral activity of the subject, such as for example the progress of dementia on the subject.

BEST MODE FOR CARRYING OUT THE INVENTION

Figure 1:
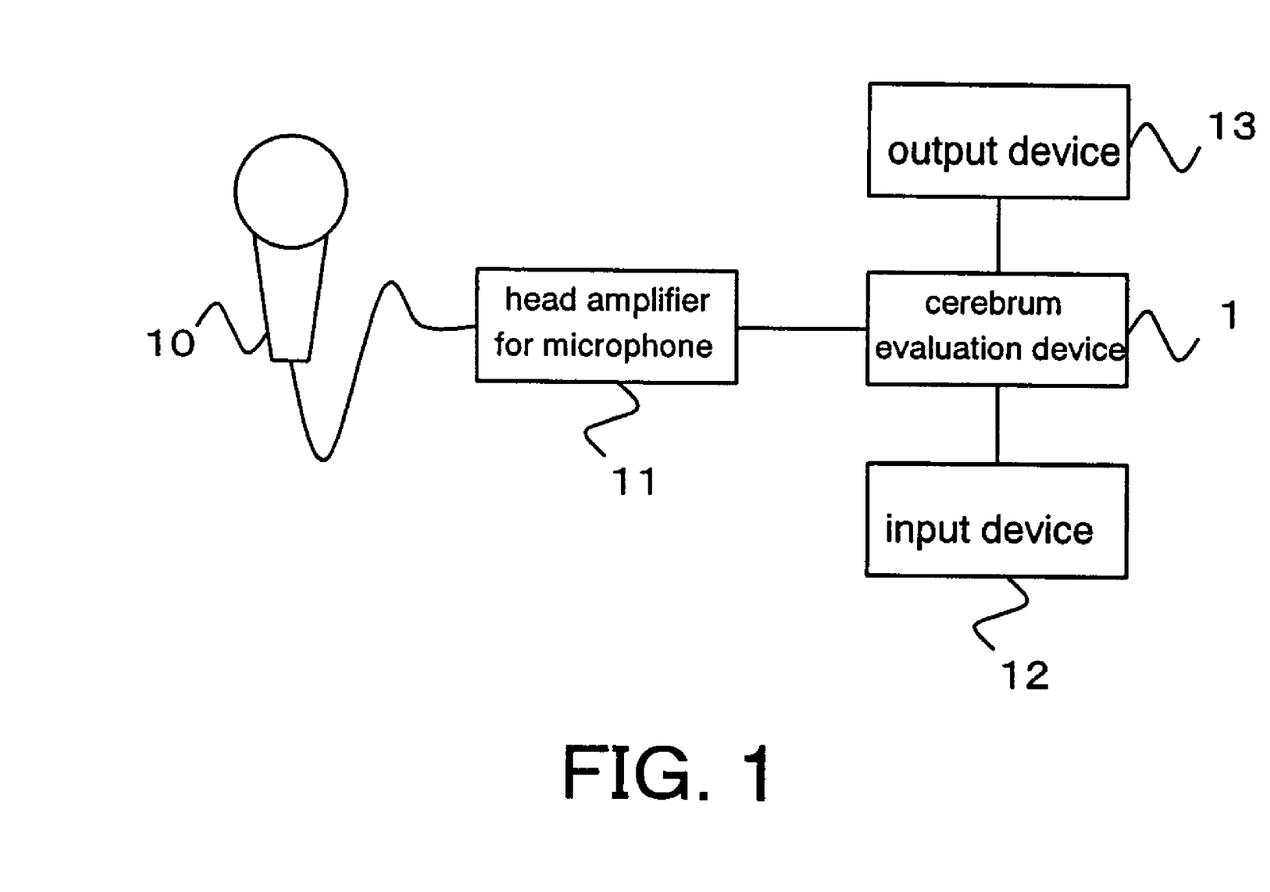
FIG. 1 is a system overview of an exemplary system arrangement including the cerebrum evaluation device of the present invention.

Now referring to FIG. 1, there is shown a schematic diagram of system overview of an exemplary system arrangement using the present invention. The system overview shown in FIG. 1 includes a cerebral evaluation device 1, a microphone 10 for acquiring the speech signal of the subject, a head amplifier 11 for microphone for amplifying the speech signal acquired by the microphone 10 to the level of normal audio line signal, an operational input device 12 such as a keyboard and a mouse for inputting to the cerebrum evaluation device 1, and an output device 13 such as a display and a printer. The microphone 10 may be alternatively any one of speech acquisition devices, which are capable of acquiring the speech voice of the subject, and the speech acquisition devices include such as an osteophonic microphone (osteophonic pickup), a radar device which measures the throat vibration with microwave or millimeter wave to obtain the signal.

Figure 2:
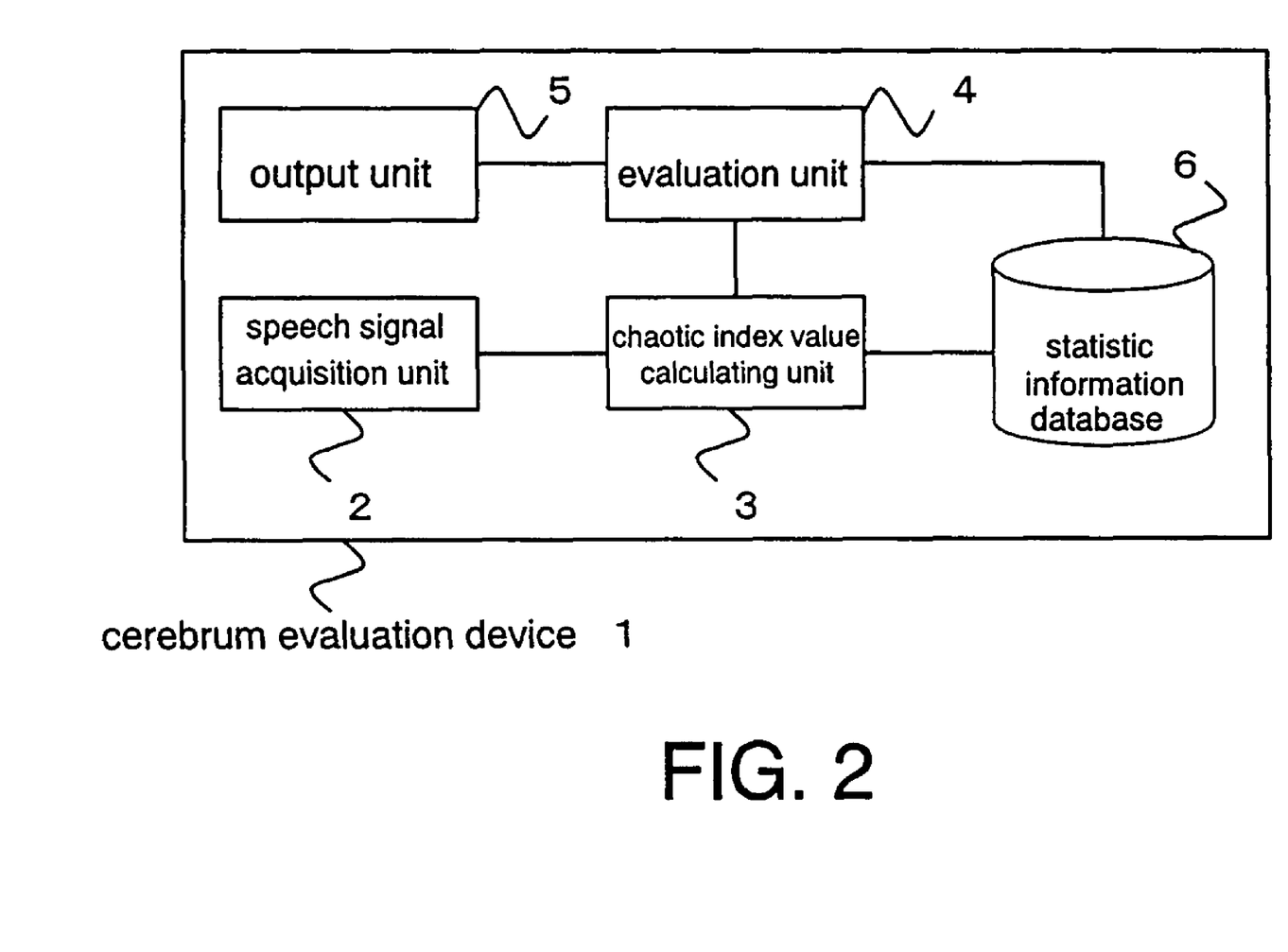
FIG. 2 is a system overview of an exemplary system arrangement of the cerebrum evaluation device of the present invention.

Now referring to FIG. 2, there is shown a schematic diagram of an exemplary system arrangement of the cerebrum evaluation device 1 in accordance with the present invention. The cerebrum evaluation device 1 includes a speech signal acquisition unit 2, a chaotic index value calculating unit 3, an evaluation unit 4, an output unit 5, and a statistic information database 6.

The speech signal acquisition unit 2 is a means for acquiring the speech signal amplified by the head amplifier 11.

The chaotic index value calculating unit 3 is a means for calculating the chaotic index value of the speech signal based on the chaotic signal processing method using the periodicity of the speech signal. The chaotic signal processing method is achievable by calculation using the method disclosed in the international application PCT/JP2003/16954, "Cerebral Function Model based on Speech Analysis" (Kakuichi Shiomi, Journal of Kansei engineering, Collected Papers of Japan Society of Kansei Engineering, vol. 4, no. 1, February 2004, p. 3-p. 12).

More specifically, the speech signal acquired by the speech signal acquisition unit 2 is sampled and cut out for a predetermined processing unit for calculating the chaotic index value corresponding to the sampled time as a microscopic chaotic index value. From the speech signal of a predetermined processing unit thus cut out the microscopic chaotic index value is calculated.

The chaotic index value of the speech signal for a predetermined period of time can be calculated as macroscopic chaotic index value, based on the microscopic chaotic index value.

Figure 5:
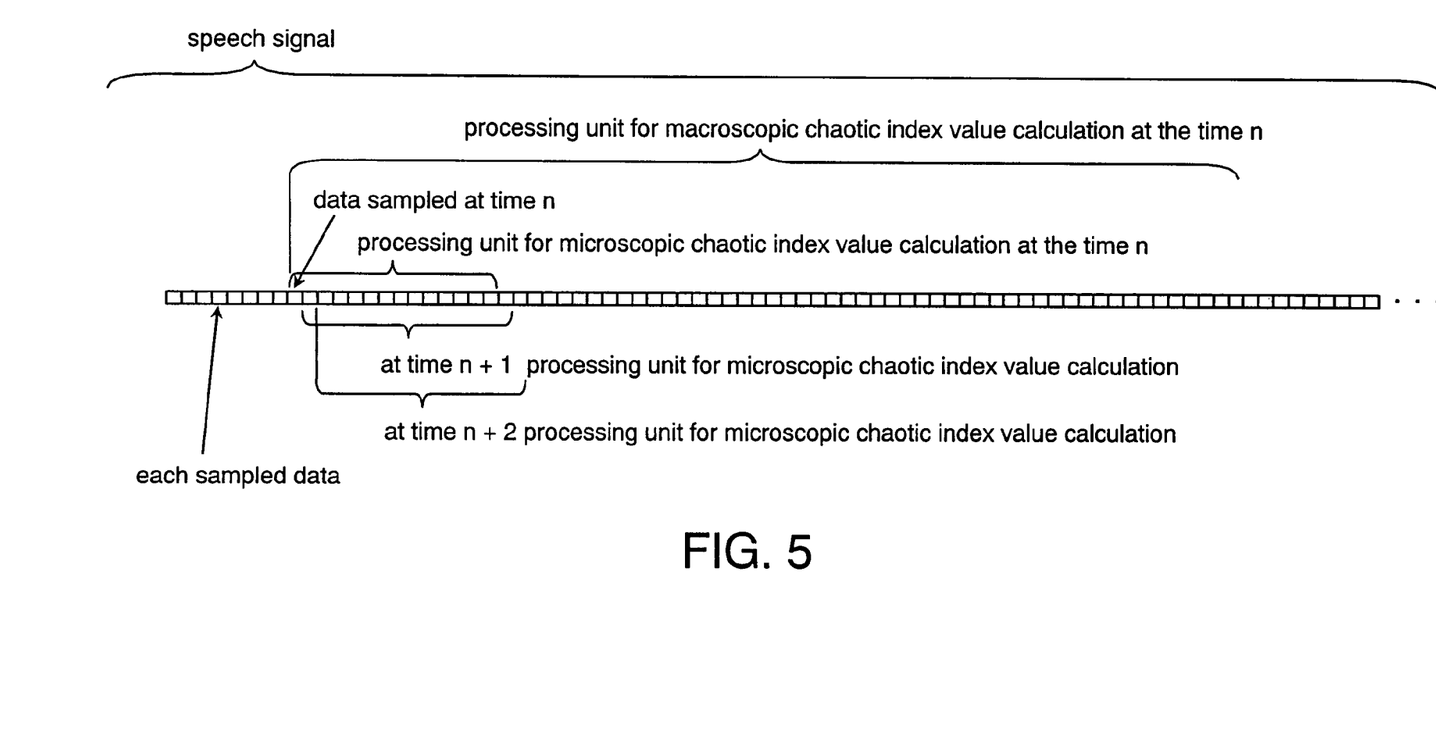
FIG. 5 is a schematic diagram illustrating the calculation of chaotic index value when calculating a chaotic index value using the periodicity of the speech signal.

The microscopic chaotic index value is the chaotic index value of the speech signal for each sampling time as described above, and the macroscopic chaotic index value is the chaotic index value for a predetermined period of time, for example the duration of a phoneme, based on the microscopic chaotic index value. This concept is shown in FIG. 5.

The evaluation unit 4 is means for evaluating the cerebral activity of the subject from the chaotic index value (macroscopic chaotic index value) of the subject calculated by the chaotic index value calculating unit 3 by referring the statistic information database 6 as described later.

The output unit 5 is means for outputting the result of evaluation by the evaluation unit 4 to the output device 13 such as a display or a printer connected to the cerebrum evaluation device 1.

The statistic information database 6 is a database storing the chaotic index values (macroscopic chaotic index values) of the speech signals of a plurality of subjects in accordance with the race, age, gender and so on of the subjects.

Figure 6:
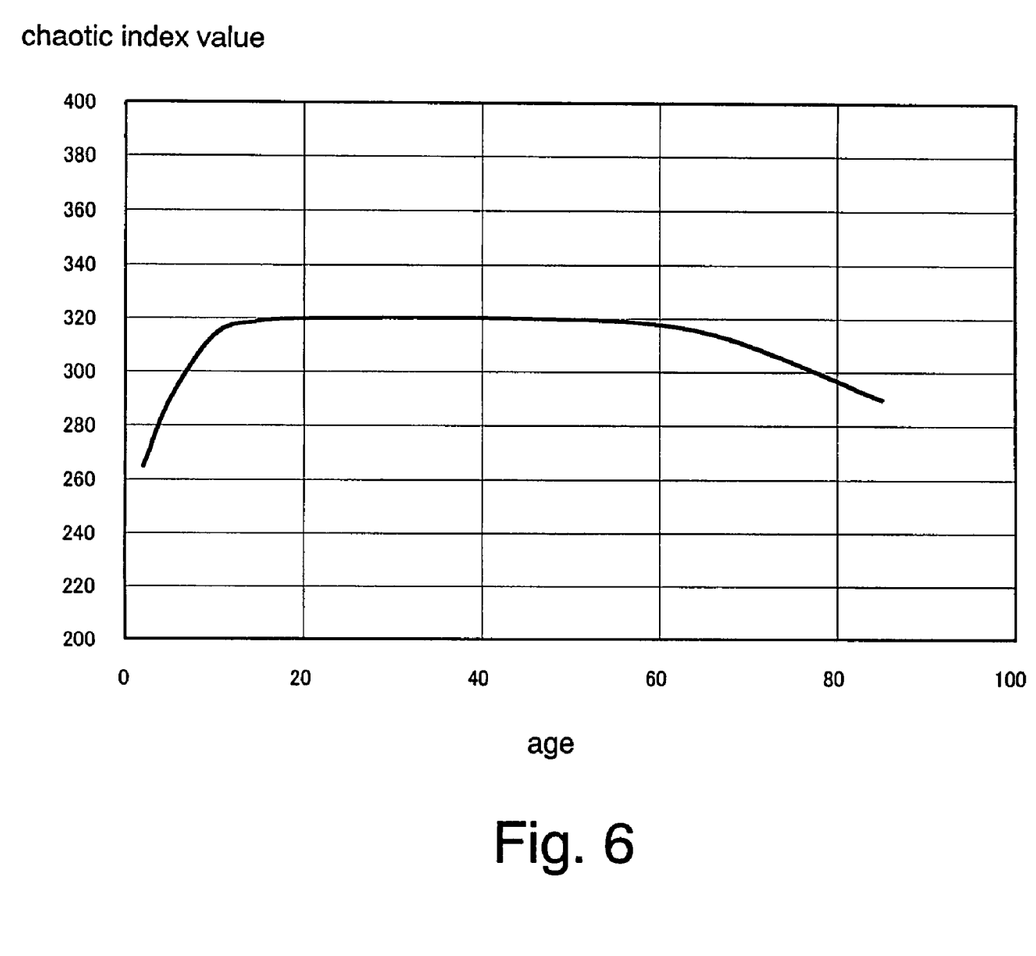
FIG. 6 is a graph illustrating the correspondence between the chaotic index value and the age.

FIG. 6 shows a graph of the chaotic index values (macroscopic chaotic index values) stored in the statistic information database 6 vs. the age. As can be seen from the graph, the index value significantly increases in the period from the infantile to about 10 years old, gradually increasing thereafter to about 20 years old, then maintains a constant value thereafter to about 50 years old. The value gradually decreases thereafter.

When comparing the chaotic index value of the subject with the chaotic index values contained in the statistic information database 6, if the subject is 60 years old but the chaotic index value is significantly lower than the chaotic index values stored in the statistic information database 6, then the subject is suspected to have a cerebral anomaly (for example cerebral function disease or dementia). Therefore the evaluation unit 4 performs such numerical comparison.

The statistic information database 6 stores the chaotic index value of the speech signal of each subject in accordance with the aging information of the subject for a long period of time, or in accordance with the information on the change of the disease along with the time if the subject has a cerebral functional disease revealed.

First Embodiment

Figure 4:
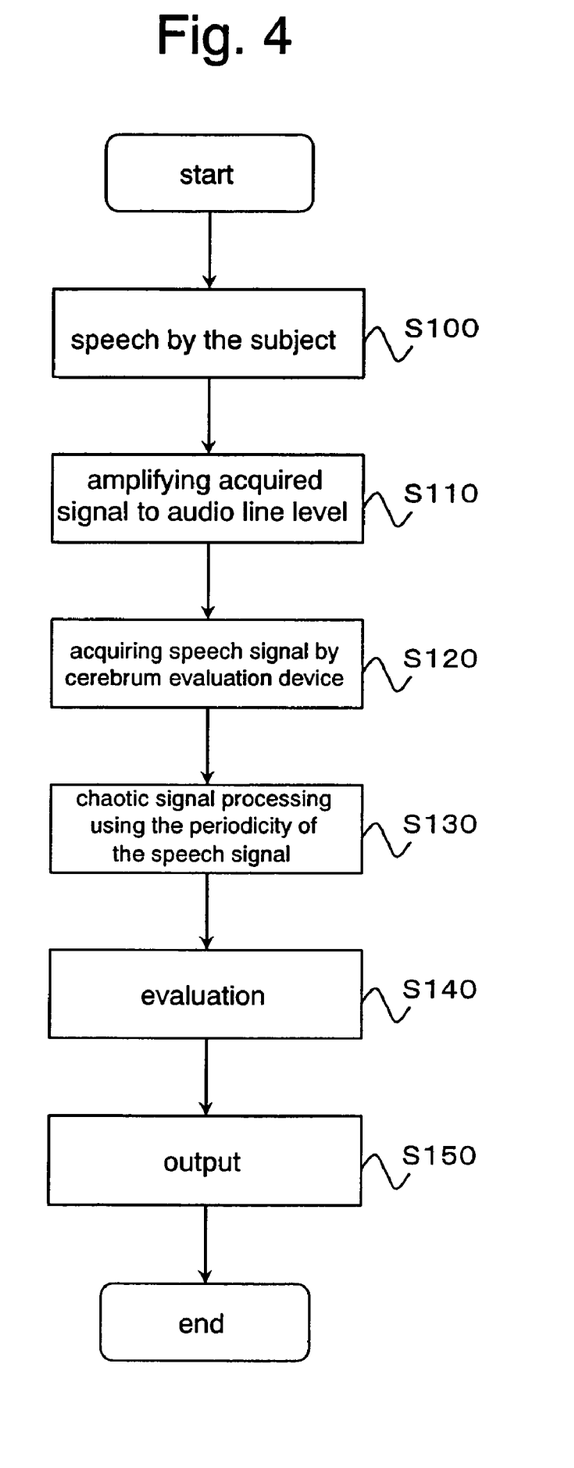
FIG. 4 is a flow chart illustrating an exemplary flow of entire process in accordance with the present invention.

An exemplary flow of process in the cerebrum evaluation device 1 in accordance with the present invention will be described herein below in greater details with reference to the flow chart shown in FIG. 4, as well as the system overview of FIG. 1 and FIG. 2.

First, the subject speaks and the speech is captured by the microphone 10 (S100). The speech signal of the speech thus obtained is amplified by the head amplifier 11 for microphone up to the level of audio line (S110).

The speech signal thus amplified is input into the cerebral evaluation device 1, and the speech signal acquisition unit 2 of the cerebrum evaluation device 1 acquires the signal (S120). If the speech signal acquired by the speech signal acquisition unit 2 is not digital signal, then an A/D converter or the like may be used to convert analog signals to digital signals.

The speech signal is sampled by the A/D converter, the chaotic index value calculating unit 3 uses the periodicity of the speech signal of the subject to calculate the chaotic index value of the subject (S130). More specifically, first, is cut out for a predetermined processing unit for calculating the chaotic index value corresponding to a given sampling time as microscopic chaotic index value. Then a microscopic chaotic index value is calculated for each speech signal of the predetermined processing unit thus cut out.

Based on the microscopic chaotic index value thus calculated, the chaotic index value of the speech signal for a predetermined period of time, namely a macroscopic chaotic index value is then calculated. The predetermined period of time may be the duration of a phoneme, for example. The macroscopic chaotic index value thus calculated is transmitted to the evaluation unit 4 as the chaotic index value output by the chaotic index value calculating unit 3.

The evaluation unit 4 refers the statistic information database 6 to evaluate the cerebral activity of the subject from the chaotic index value of the subject calculated by the chaotic index value calculating unit 3 (S140). The statistic information database 6 stores the chaotic index values of the speech signals of a plurality of subjects in accordance with their race, age, gender and so on. The evaluation unit 4 then compares the chaotic index value of the subject calculated in S130 with the chaotic index values stored in the statistic information database 6 for the purpose of evaluation.

For example, when in the statistic information database 6, the chaotic index values of a plurality of subjects are stored along with the age, if the age and the chaotic index value of the subject to be evaluated is compared with the ages and chaotic index values stored in the statistic information database 6, the cerebral activity of the subject to be evaluated can be evaluated whether to comply with the statistic information of the age of the subject.

When the correspondence between the chaotic index value and the age stored in the statistic information database 6 is as shown in FIG. 6, if the subject is 60 years old but the chaotic index value of the subject is significantly lower than the chaotic index value stored in the statistic information database 6, then the subject is suspected to have a cerebral anomaly (for example a cerebral functional disease or dementia). Such numerical comparison is performed by the evaluation unit 4.

The result of such evaluation is output from the output unit 5 to the output device 13 (S150). For example, in the example as have been described above, the chaotic index value of the subject may be output to the output device 13, or displayed as the overlay on a graph shown in FIG. 6, or displayed as a message telling that "cerebral anomaly is detected".

By storing the chaotic index value as the processing result of the speech signal of each subject along with the aging information of the subject for a long period of time in the statistic information database 6, or along with the information on revelatory change of the disease state if the subject is revealed to have a cerebral functional disease, the onset of a cerebral functional disease of the subject or the progress of the disease can be evaluated from the change of the chaotic index value of the subject along with the time.

Second Embodiment

Figure 3:
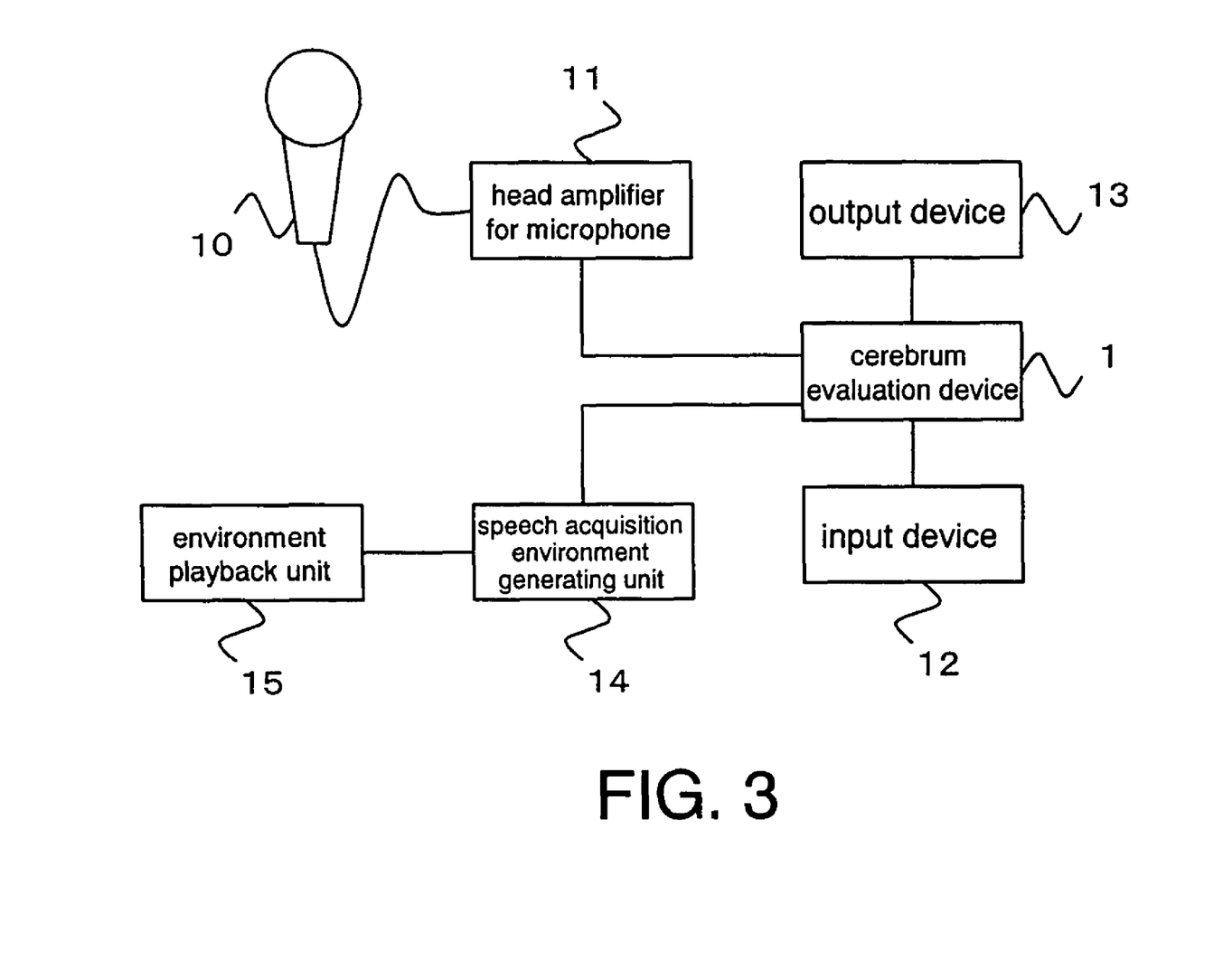
FIG. 3 is another system overview of another exemplary system arrangement including the cerebrum evaluation device of the present invention.

FIG. 3 shows another exemplary system arrangement in accordance with the present invention. In the system shown in FIG. 3, there are a speech acquisition environment generating unit 14 for controlling the acquisition environment of the speech and an environment playback unit 15 for playing back the environment in addition to the system arrangement shown in FIG. 1.

The speech acquisition environment generating unit 14 is a device achieving the speech acquisition environment similar to the eye test or audiometry, and the environment playback unit 15 is a display for replaying pictures or images, or a speaker or a headphone for replaying the speech voice.

By using the speech acquisition environment generating unit 14, the subject focuses on the picture or image and speech displayed on the environment playback unit 15 to allow the speech uttered by the subject to be made homogeneous. This may improve the precision of the chaotic index value calculated by the cerebrum evaluation device 1.

For example, when the environment playback unit 15 is served instead of the output device 13, the subject is instructed to watch the environment playback unit 15, and the speech acquisition environment generating unit 14 displays a picture, illustration, silhouette of an object, or eye chart on the environment playback unit 15. The subject is asked to recognize by speech and the microphone 10 acquires the speech.

For instance, the subject is asked "what can you see?", then the subject responds "a puppy". At that time the microphone 10 acquires the speech as the object to be analyzed.

When the environment playback unit 15 is used as a sound player device such as a headphone or a speaker, the speech acquisition environment generating unit 14 plays the sound such as glass breaking, running train, wave sound, varying from a very small sound at first then gradually larger sound level, or intermittently playing the sound and the subject is asked to recognize verbally the sound.

For instance, the subject is asked "what can you hear", then the subject responds "a siren of a police car" at that moment the speech is acquired by the microphone 10 as the object to be analyzed.

The speech signal thus acquired is used in the cerebral evaluation device 1 to calculate and evaluate the chaotic index value.

The environment playback unit 15 in the above embodiment may use, in addition to the picture, image, and sound, the smell, taste, vibration and the like as the object on which the subject concentrate.

The means and database in accordance with the present invention are solely distinguished by logical function, these may physically or virtually share the same area. The term database may be any one of storage means for storing any data, and a data file may be used instead of the database, therefore the term database includes a data file.

It is appreciated that, when embodying the present invention a software program stored in a recording medium which achieves the functionality of the preferred embodiment may be provided to a system, and the computer in the system reads out the program stored in the recording medium and executes the program to achieve the present invention.

In this case the program itself which is read out from the recording medium achieves the functionality of the preferred embodiment, therefore the recording medium storing the program constitutes part of the present invention.

Some examples of recording medium for supplying the program may include for example, a magnetic disk, a hard disk, an optical disk, a magneto-optical disk, a magnetic tape, a nonvolatile memory card, and the like.

The functionality of the preferred embodiment described above may be achieved not only by executing the program read out by the computer, but also by an operating system running on the computer which executes all or part of the actual processing, based on the instruction of the program, to thereby achieve functionality of the preferred embodiment.

In addition, the program read out from the recording medium may be written into a nonvolatile or volatile storage means in an expansion card inserted in the computer or an expansion unit connected to the computer, then the processing unit of the expansion card or the expansion unit executes all or part of the actual processing based on the instruction of the program to thereby achieve the functionality of the preferred embodiment as have been described above.

INDUSTRIAL APPLICABILITY

Using the present invention allows measuring the cerebral activity of a subject from the speech signal while the subject does not recognize as burden. By comparing the measured value with the statistic data of the cerebral activity previously recorded, the level of the cerebral activity of the subject for example the progress of the dementia of the subject can be diagnosed.

REFERENCE NUMERALS 1 cerebrum evaluation device
2 speech signal acquisition unit
3 chaotic index value calculating unit
4 evaluation unit
5 output unit
6 statistic information database
10 microphone
11 head amplifier for microphone
12 input device
13 output device
14 speech acquisition environment generating unit
15 environment playback unit

What is claimed is:

1. A cerebrum evaluation apparatus for evaluating a cerebral state by analyzing a speech signal of a target subject, comprising:
a statistic information database containing chaotic index values of speech signals of a plurality of reference subjects;

a speech signal acquisition device for acquiring said speech signal; and a processor comprising:

a chaotic index value calculating unit for calculating a chaotic index value of said speech signal by chaotic signal processing using a periodicity of said acquired speech signal;

an evaluation unit for evaluating the cerebral state of said target subject from said calculated chaotic index value by referring to said statistic information database; and an output unit for outputting a result evaluated by said evaluation unit.

2. A cerebrum evaluation apparatus for evaluating a cerebral state by analyzing a speech signal of a target subject, comprising:

a statistic information database containing time-sequential chaotic index values of the speech signal of said target subject;

a speech signal acquisition device for acquiring said speech signal; and a processor comprising:

a chaotic index value calculating unit for calculating a chaotic index value of said speech signal by chaotic signal processing using a periodicity of said acquired speech signal;

an evaluation unit for evaluating the cerebral state of said target subject from said calculated chaotic index value by referring to said statistic information database; and an output unit for outputting a result evaluated by said evaluation unit.

3. A cerebrum evaluation apparatus in accordance with claim 1 or claim 2, wherein said speech signal acquisition device comprises an A/D converter for sampling the acquired speech signal.

4. A cerebrum evaluation apparatus in accordance with claim 1, wherein:

said statistic information database stores the chaotic index values of speech signals of said reference subjects in correspondence with one or more of a race, an age, or a gender of said reference subjects; and said evaluation unit evaluates the cerebral state of said target subject by comparing the chaotic index value of the target subject and one or more of a race, an age, or a gender of the target subject with the chaotic index values and the race, the age, or the gender stored in said statistic information database.

5. A cerebrum evaluation apparatus in accordance with claim 2, wherein:

said statistic information database stores the chaotic index values of speech signals of said target subject in correspondence with aging information of said target subject and a change of cerebral functional disease along with time; and said evaluation unit evaluates the cerebral state of said target subject based on the change along with time of the chaotic index value of said target subject.

6. A cerebrum evaluation apparatus in accordance with claim 1 or claim 2, further comprising:

a speech acquisition environment generating device for controlling an environment during acquisition of said speech signal; and an environment playback device for playing back the environment specified by said speech acquisition environment generating unit, wherein said speech acquisition environment generating device determines, as the environment for said target subject, one or more of a picture, an image, or a sound, and wherein said environment playback device plays back said determined environment.

7. A non-transitory computer-readable medium tangibly embodied in a storage device, comprising:

a statistic information database stored in the storage device and containing chaotic index values of speech signals of a plurality of subjects; and a plurality of instructions which, when executed by a computer, perform the following steps:

calculating a chaotic index value of the speech signal, acquired by a speech signal acquisition unit, by chaotic signal processing using the periodicity of the acquired speech signal; and evaluating a cerebral state of the subject from the calculated chaotic index value by referring to the statistic information database.

* * * * *